United States Patent
Cha et al.

(10) Patent No.: US 9,675,629 B2
(45) Date of Patent: Jun. 13, 2017

(54) PH-RESPONSIVE NANOPARTICLE USING MUSSEL ADHESIVE PROTEIN FOR DRUG DELIVERY AND METHOD FOR PREPARING THE SAME

(71) Applicant: POSTECH ACADEMY-INDUSTRY FOUNDATION, Pohang-si, Gyeongsangbuk-do (KR)

(72) Inventors: Hyung Joon Cha, Pohang-si (KR); Bum Jin Kim, Pohang-si (KR); Ho gyun Cheong, Incheon (KR)

(73) Assignee: Postech Academy-Industry Foundation, Gyeongsangbuk-Do (KR)

( * ) Notice: Subject to any disclaimer, the term of this patent is extended or adjusted under 35 U.S.C. 154(b) by 0 days.

(21) Appl. No.: 15/000,551

(22) Filed: Jan. 19, 2016

(65) Prior Publication Data
US 2016/0263136 A1   Sep. 15, 2016

(30) Foreign Application Priority Data

Mar. 13, 2015 (KR) ........................ 10-2015-0035270

(51) Int. Cl.
| | | |
|---|---|---|
| *A61K 9/51* | (2006.01) | |
| *A61K 31/704* | (2006.01) | |
| *A61K 9/16* | (2006.01) | |
| *A61K 38/00* | (2006.01) | |

(52) U.S. Cl.
CPC .......... *A61K 31/704* (2013.01); *A61K 9/1617* (2013.01); *A61K 9/1658* (2013.01); *A61K 9/1682* (2013.01); *A61K 9/5169* (2013.01); *A61K 38/00* (2013.01)

(58) Field of Classification Search
CPC ...... A61K 9/14; A61K 9/1617; A61K 9/1641; A61K 9/1658; A61K 9/1682; A61K 9/51; A61K 9/5107; A61K 9/5123; A61K 9/513; A61K 9/5146; A61K 9/5169
See application file for complete search history.

(56) References Cited

U.S. PATENT DOCUMENTS

2005/0084456 A1* 4/2005 Tang ................... A61K 9/5138
                                                  424/46
2014/0023594 A1* 1/2014 Park ................... A61K 49/1857
                                                  424/9.322

OTHER PUBLICATIONS

Kim et al. Mussel-Inspired Protein Nanoparticles Containing Iron(IIII)-DOPA Complexes for pH-Responsive Drug Delivery. Angewandte Chemie International Edition. May 12, 2015, vol. 54, pp. 7318-7322.*
Qiao et al. Kidney-specific drug delivery system for renal fibrosis based on coordination-driven assembly of catechol-derived chitosan. Biomaterials. May 23, 2014, vol. 35, pp. 7157-7171.*
Kim, Bum Jin et al., "Mussel-inspired adhesive protein-based electrospun nanofibers reinforced by (Fe(III)-DOPA complexation" J. Mater Chem. B. (2015), vol. 3, pp. 112-118.
Kim, Bum Jin et al., "Mussel-mimetic protein-based adhesive hydrogel" Biomacromolecules (2014), vol. 15, pp. 1579-1585.
Zeng, Hongbo et al., "Strong reversible Fe3+-mediated bridging between dopa-containing protein films in water" PNAS (2010), vol. 107(29), pp. 12850-12853.
Sridhar, Radhakrishnan et al., "Electrosprayed nanoparticles for drug delivery and pharmaceutical applications" Biomatter (2013), vol. 3(3), pp. e24281-1-e24281-12.
Harrington, Matthew J. et al., "Iron-clad fibers: a metal-based biological strategy for hard flexible coatings" Science (2010), vol. 328, pp. 216-220.

* cited by examiner

*Primary Examiner* — Jeffrey E Russel
(74) *Attorney, Agent, or Firm* — McDonnell Boehnen Hulbert & Berghoff LLP

(57) ABSTRACT

The present invention relates to a pH-responsive metal-catechol derivative nanoparticle for drug delivery based on a mussel adhesive protein, particularly Fe(III)-DOPA nanoparticle, and a method for preparing the same. A nanoparticle for drug delivery according to the present invention is prepared using a pH responsive substance, catechol derivative-metal complex, particularly Fe(III)-DOPA complex, based on a mussel adhesive protein. Thereby, the present invention has excellent biocompatibility, is capable of easily and quickly penetrating into a target cell, and releases a loaded drug under acidic conditions, which enables to selectively deliver a drug to a specific disease having an acidic environment.

16 Claims, 4 Drawing Sheets

PH-RESPONSIVE NANOPARTICLE USING MUSSEL ADHESIVE PROTEIN FOR DRUG DELIVERY AND METHOD FOR PREPARING THE SAME

TECHNICAL FIELD

The present invention relates to pH-responsive metal-catechol derivative nanoparticles for drug delivery based on mussel adhesive proteins, particularly Fe(III)-DOPA nanoparticles, and methods for preparing the same.

BACKGROUND ART

Nanoparticles have been considered as promising drug delivery carriers for clinically-applicable pharmaceutics with help of their drug tolerability, circulation half-life, and delivery efficiency in the past decades. Nowadays, multifunctionalities such as sustained release, molecular targeting, and environmental reactions have been adopted for development of functionally-improved nanoparticles. Especially, response behaviors against various types of physical and chemical signals have been introduced into nanoparticles as a design strategy for rendering them release drugs when exposed to particular external stimulus. Among several environmental stimuli, pH has been widely exploited as one of the important chemical cues to design responsive nanoparticles. Most applicable target of those pH-responsive nanoparticles at cellular level is intracellular delivery of anti-cancer drugs through acidified endosomal compartments where pH level rapidly drops to under 6. Although endosomal acidification may elicit harmful effect on delivered macromolecules such as DNAs, RNAs, and proteins, it can also be utilized as a chance for their endosomal escape and effective delivery. Moreover, because overcoming the endosomal acidification has been considered as a major hurdle for many types of anti-cancer drugs to be delivered as highly concentrated manner in a cytosol of cancer cells, pH-responsive drug delivery ability of nanoparticles can be a great advantage for cancer therapy applications. Also, various kinds of pH-induced cleavage chemistries of polymeric materials and diverse formulations of nanoparticles have been applied to realize the endosomal escape and cytosolic drug release.

Metal coordination complexes have been found in many biological materials (e.g., mussel fiber, spider's fangs, and squid beak), playing major roles in their tremendous mechanical, adhesive, and frictional performances. Proteinaceous cuticles covered on mussel byssal threads are the representative example, in which metal-catecholic coordinations are discovered as a form of complex between Fe(III) and 3,4-dihydroxyphenylalanine (DOPA), and act as a key cross-linking mediator for their outstanding mechanical properties. Moreover, those Fe(III)-DOPA complexes are known to be as strong as covalent bonding, and their multiple bidentate stoichiometry can be altered by environmental pH to form mono-, bis-, and tris-Fe(III)-DOPA cross-links. Using those characteristics, mussel-inspired biomaterials containing Fe(III)-DOPA complexes with high mechanical performance and self-healing property have been developed for biomedical applications. In particular, Fe(III)-DOPA complexes have been applied to the field of synthesis of nanoparticles.

However, most of the works have been focused on exploiting Fe(III)-DOPA complexes for surface modification of metal oxide nanoparticles, introduction of stabilizing nanoparticles through the surface exposure of polyethylene glycol, and altering magnetic properties of iron oxide nanoparticles, but they have not been applied for synthesis of nanoparticles to perform environmentally sensitive drug delivery.

SUMMARY OF INVENTION

While searching for pH-responsive drug delivery carriers, the present inventors found that a metal-catechol derivative complex based on a mussel adhesive protein, particularly a Fe(III)-DOPA complex nanoparticle, has excellent biocompatibility, is capable of easily and quickly penetrating into a target cell, and releases a loaded drug under acidic conditions, which enables to selectively deliver a drug to a specific disease having an acidic environment. Thereby, the present inventors completed the present invention.

The present invention aims to provide a metal-catechol derivative nanoparticle based on a mussel adhesive protein, particularly a Fe(III)-DOPA nanoparticle, and a method for preparing the same.

To achieve the above objects, the present invention provides a pH-responsive nanoparticle for drug delivery, including a catechol derivative; a metal capable of forming a coordinate bond with the catechol derivative; and a drug.

Also, the present invention provides an anti-cancer drug including the pH-responsive nanoparticle for drug delivery.

Also, the present invention provides a drug delivery carrier including the pH-responsive nanoparticle for drug delivery.

Also, the present invention provides a method for preparing a pH-responsive nanoparticle for drug delivery, including (1) mixing a mussel adhesive protein of which a tyrosine residue is converted into a catechol derivative and a metal capable of forming a coordinate bond; and (2) mixing a drug with the mixture, followed by electrospraying.

Hereinafter, the present invention is described in detail.

The present invention provides a pH-responsive nanoparticle for drug delivery, including a catechol derivative; a metal capable of forming a coordinate bond with the catechol derivative; and a drug.

The catechol derivative is preferably formed by converting a tyrosine residue of a mussel adhesive protein.

Examples of the mussel adhesive protein, which is an adhesive protein originating from a mussel, preferably include a mussel adhesive protein originating from *Mytilus edulis*, *Mytilus galloprovincialis* or *Mytilus coruscus* or variants thereof, but are not limited thereto.

The mussel adhesive protein may be *Mytilus edulis* foot protein (Mefp)-1, *Mytilus galloprovincialis* foot protein (Mgfp)-1, *Mytilus coruscus* foot protein (Mcfp)-1, Mefp-2, Mefp-3, Mgfp-3, and Mgfp-5, originating from each of the mussel species or variants thereof, preferably a protein selected from the group consisting of foot protein (fp)-1 (SEQ ID NO: 1), fp-2 (SEQ ID NO:5), fp-3 (SEQ ID NO: 6), fp-4 (SEQ ID NO: 7), fp-5 (SEQ ID NO: 8), and fp-6 (SEQ ID NO: 9), a fusion protein where two or more types of proteins are fused, or variants of the protein, but is not limited thereto. Further, the mussel adhesive protein of the present invention includes all of the mussel adhesive proteins described in WO2006/107183 or WO2005/092920. The mussel adhesive protein preferably includes a fusion protein, such as fp-151 (SEQ ID NO: 10), fp-131 (SEQ ID NO: 12), fp-353 (SEQ ID NO: 13), fp-153 (SEQ ID NO: 14), fp-351 (SEQ ID NO: 15), or the like, but is not limited thereto. In addition, the mussel adhesive protein of the present invention may include a polypeptide where decapeptide (SEQ ID NO: 2) that repeats about 80 times in fp-1 is linked 1 to 12 times or more consecutively, preferably a fp-1 variant polypeptide (SEQ ID NO: 3) where decapeptide of SEQ ID NO: 2 is linked 12 times consecutively, but is not limited thereto.

Also, under the condition that the mussel adhesive protein maintains adhesion of the mussel adhesive protein, the mussel adhesive protein of the present invention may include an additional sequence to the carboxyl terminus or the amino terminus of the mussel adhesive protein or substitute some amino acids with other amino acids. Preferably, the mussel adhesive protein may link a polypeptide including 3 to 25 amino acids with Arg-Gly-Asp (RGD) at the carboxyl terminus or the amino terminus of the mussel adhesive protein, but is not limited thereto. The 3 to 25 amino acids with the RGD is preferably, but not limited to, at least one selected from the group consisting of Arg-Gly-Asp (RGD, SEQ ID NO: 16), Arg-Gly-Asp-Ser (RGDS, SEQ ID NO: 17), Arg-Gly-Asp-Cys (RGDC, SEQ ID NO: 18), Arg-Gly-Asp-Val (RGDV, SEQ ID NO: 19), Arg-Gly-Asp-Ser-Pro-Ala-Ser-Ser-Lys-Pro (RGDSPASSKP, SEQ ID NO: 20), Gly-Arg-Gly-Asp-Ser (GRGDS, SEQ ID NO: 21), Gly-Arg-Gly-Asp-Thr-Pro (GRGDTP, SEQ ID NO: 22), Gly-Arg-Gly-Asp-Ser-Pro (GRGDSP, SEQ ID NO: 23), Gly-Arg-Gly-Asp-Ser-Pro-Cys (GRGDSPC, SEQ ID NO: 24), and Tyr-Arg-Gly-Asp-Ser (YRGDS, SEQ ID NO: 25).

Examples of the variant of the mussel adhesive protein to which a polypeptide including 3 to 25 amino acids with RGD at the carboxyl terminus or the amino terminal of the mussel adhesive protein is preferably, but not limited to, a fp-1 variant-RGD polypeptide including the amino acid sequence of SEQ ID NO: 4 or a fp-151-RGD polypeptide including the amino acid sequence of SEQ ID NO: 11.

Preferably, 10 to 100% of the total tyrosine residues in the mussel adhesive protein are converted into the catechol derivative. Tyrosine forms about 20 to 30% of the total amino acid sequences of almost all of the mussel adhesive proteins. Tyrosine in a natural mussel adhesive protein is converted into a catechol derivative DOPA by adding an OH group through a hydration process. However, for a mussel adhesive protein produced in *Escherichia coli*, tyrosine residues are not converted, and thus, it is preferable to conduct a modification reaction of converting tyrosine into DOPA by a separate enzyme and chemical process. For a method for modifying tyrosine residues included in the mussel adhesive protein, any known methods in the art may be used without specific limitation. As a preferable example, tyrosine residues may be modified to DOPA residues using tyrosinase. According to an embodiment of the present invention, a mussel adhesive protein satisfying the DOPA conversion rate may be produced through an in vitro enzymatic reaction using mushroom tyrosinase.

The catechol derivative, which is a compound including a dihydroxyl group, is capable of forming a coordinate bond with a metal. Specifically, examples of the catechol derivative may include 3,4-dihydroxyphenylalanine (DOPA), Dopa o-quinone, dopamine, norepinephrine, epepinephrine, epigallocatechin gallate, and derivatives thereof, preferably DOPA.

The metal capable of forming a coordinate bond, which is any metal capable of forming a coordinate bond with the catechol derivative, may be a typical metal or a transition metal. Examples of the metal may include titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum, and gold, which are capable of forming a coordinate bond, preferably Fe(III).

The catechol derivative and the metal form a coordinate bond to obtain a metal-catechol derivative complex. The metal-catechol derivative complex may be preferably a Fe(III)-DOPA complex. According to an embodiment of the present invention, DOPA and Fe(III) which are present in a mussel adhesive protein form cross-linking via coordinate bonds, and are excellent in biocompatibility since DOPA and Fe(III) are already present in human bodies.

The drug may be a low molecular weight drug, a genetic drug, a protein drug, an antibody drug, a synthetic compound drug, or a combination thereof, but is not limited thereto. Specifically, examples of the low molecular weight drug may include doxorubicin, dactinomycin, mitomycin, bleomycin, cytarabine, azaserine, mechlorethamine, cyclophosphamide, triethylenemelanin, treosulfan, retinoic acid, vinblastine, vincristine, aspirin, salicylate, ibuprofen, flurbiprofen, piroxicam, naproxen, fenoprofen, indomethacin, phenylbutazone, methotrexate, mechlorethamine, dexamethasone, prednisolone, celecoxib, valdecoxib, nimesulide, cortisone, or corticosteroid. Examples of the genetic drug may include small interfering RNA (siRNA), small hairpin RNA (shRNA), microRNA (miRNA), or plasmid DNA. Examples of the protein drug may include monoclonal antibody-based drugs, trastuzumab, rituximab, bevacizumab, cetuximab, bortezomib, erlotinib, gefitinib, imatinib mesylate, and sunitinib; enzyme-based drug, L-asparaginase; hormone-based drugs, triptorelin acetate, megestrol acetate, flutamide, bicalutamide, and goserelin; cytochrome c, p53 protein, etc. Particularly, the drugs may be anti-cancer drugs including doxorubicin, paclitaxel, docetaxel, cisplatin, carboplatin, 5-FU, etoposide, or camptothecin, which has anti-cancer effects.

The drug-loaded complex nanoparticle of the present invention is indissoluble under alkali conditions, i.e., at pH 7.0 or higher, but dissolved under acidic conditions, i.e., at pH 0.1 to 6.5 and releases a drug. The drug-loaded complex nanoparticle is indissoluble in bloodstream at pH 7.4 and show stable properties, whereas they are readily dissolved in lower pH environments, in cancer tissue (at pH up to 6.3), endosome (at pH up to 5.0) and lysosome (at pH up to 4.5) and thus induce the release of the drug loaded in complex nanoparticle.

The nanoparticle may have a mean diameter of 80 to 130 nm, preferably 110 nm. The nanoparticle with this size allows the nano-complex to appropriately migrate to a target cell and to be delivered via various routes including injection, oral delivery, or skin delivery, when introduced into human bodies. The loaded drug may be delivered to humans or other mammals in a disease state or with symptoms which may be effectively treated by the drug, suitably via injection or other ways, preferably via parenteral delivery. Examples of the parenteral delivery route include intramuscular, intraperitoneal, intraabdominal, subcutaneous, intravenous and intraarterial routes. Accordingly, the complex nanoparticle of the present invention may be formulated into injection formulation, representatively. The injectable complex nanoparticle of the present invention may be injected or inserted into the bodies of humans or other mammals via any suitable way, preferably injection with subcutaneous needles. For example, the complex nanoparticle of the present invention may be administered via injection or other ways, to artery, vein, urogenital organs, under the skin, muscle, under the skin, skull, pericardium, pleura, or other body cavities or available spaces. Or, the complex nanoparticle of the present invention may be introduced, via a catheter or a syringe during an operation, surgical treatment, diagnosis or interventional procedure, into, for example, joint during arthroscopic surgery, urogenital organs, vas, palate, pleura, or any body cavities or available spaces.

The nanoparticle may be used for treating diseases including cancer, Alzheimer's disease, cardiovascular disorders, rheumarthritis, and osteoporosis, preferably cancer, but is not limited thereto. The nanoparticle may be used unlimitedly for any diseases, if the drug can be released thereagainst in an acidic environment at pH 7.0 or lower. The disease may be any cancers occurring in mammals, particularly humans. Specifically, the disease may be a solid cancer occurring in skin, digestive organs, urogenital organs, respiratory organs, hematopoietic system, brain, nervous system, etc. Examples of the solid cancer may include skin cancer, melanoma, stomach cancer, esophageal cancer, colon cancer, colorectal cancer, pancreatic cancer, colorectal cancer, rectal cancer, cholangiocarcinoma, liver cancer, brain tumor, leukemia, osteosarcoma, bone cancer, breast cancer, thyroid cancer, lung adenocarcinoma, uterine cancer, uterine cervix cancer, endometrial cancer, prostate cancer, head and neck cancer, bladder cancer, endocrine adenocarcinoma, urethra cancer, ovarian cancer, testis cancer, kidney cancer, bladder cancer, prostate cancer, or lymphoma, preferably, uterine cancer, uterine cervix cancer, endometrial cancer, melanoma, or breast cancer.

Also, the present invention provides an anti-cancer drug including the pH-responsive nanoparticle for drug delivery.

Also, the present invention provides a drug delivery carrier including the pH-responsive nanoparticle for drug delivery.

Also, the present invention provides a method for preparing a pH-responsive nanoparticle for drug delivery, including the steps of (1) mixing a mussel adhesive protein of which a tyrosine residue is converted into a catechol derivative and a metal capable of forming a coordinate bond; and (2) mixing a drug with the mixture, followed by electrospraying.

In the step (1), the mussel adhesive protein of which the tyrosine residue is converted into the catechol derivative is cross-linked with the metal through coordinate bonding.

The mussel adhesive protein and the drug are mixed in various ratios, and then complex nanoparticle may be prepared by electrospraying. For example, the mussel adhesive protein and the drug are mixed in a mixing ratio of 1:0.1 to 1:10 (w/w), preferably 1:1 to 1:4 (w/w), and then complex nanoparticle may be prepared by electrospraying.

Examples of the catechol derivative may include 3,4-dihydroxyphenylalanine (DOPA), Dopa o-quinone, dopamine, norepinephrine, epepinephrin, epigallocatechin gallate, and derivatives thereof, preferably DOPA. Examples of the metal capable of forming a coordinate bond may include titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum, and gold, which are capable of forming a coordinate bond, preferably Fe(III).

The DOPA is known to form mono-, bis-, or tris-cross-links while linking to Fe(III) metals depending on pH. Also, the DOPA is known to exhibit unique colors of Fe(III)-DOPA complexes depending on bonding aspects. According to an embodiment of the present invention, a reagent including Fe(III), for example, FeCl$_3$, may be used for providing Fe(III) metals. Preferably, FeCl$_3$ solution may be added so that the molar ratio of Fe(III) to DOPA is 1:3 or a ratio with less Fe(III).

In the step (2), the drug is mixed with the mixture of step (1), and then complex nanoparticle is prepared by electrospraying the mixture. Electrospraying is a technique forming nanoparticles using electrical attraction and repulsion occurring when charging a polymer solution or a molten polymer with a predetermined voltage. According to electrospraying, nanoparticles having various diameters of several nm to thousands nm can be prepared with simple equipment and may be applied to a variety of substances. According to an embodiment of the present invention, in order to conduct the electrospraying, the mussel adhesive protein, Fe(III), and drug may be dissolved in a water-based solvent. The use of the water-based solvent, instead of an organic solvent, may eliminate a toxic effect of the solvent left during the electrospraying. In order to increase evaporative properties of the water-based solvent, an organic solvent may be additionally mixed, and preferably, 60 to 80% (v/v) of ethanol with respect to distilled water may be additionally mixed.

The doxorubicin (DOX)-loaded Fe(III)-DOPA complex nanoparticle according to the present invention has excellent biocompatibility and exhibits cytotoxicity effect on cancer cells through effective cellular uptakes and their cytosolic release.

The nanoparticle for drug delivery according to the present invention is prepared using the pH-responsive metal-catechol derivative based on the mussel adhesive protein, particularly Fe(III)-DOPA complex, thereby having excellent biocompatibility, easily and quickly penetrating into a target cell, and releasing a loaded drug under acidic conditions, which enables to selectively deliver a drug to a specific disease having an acidic environment.

DETAILED DESCRIPTION FOR CARRYING OUT THE INVENTION

Hereinafter, preferred examples are provided for helping better understand the present invention. The following examples are provided for illustrative purposes only, and those skilled in the art will appreciate that the present invention is not limited to the scope of the examples.

Example 1. Preparation of Doxorubicin (DOX)-Loaded Fe(β)-DOPA Complex Nanoparticles 1.1 Preparation of DOPA-Modified Recombinant Mussel Adhesive Protein (mfp-1)

Mussel adhesive protein fp-1 (*Mytilus* mussel foot protein type 1) variant (SEQ ID NO: 3) composed of 12 times repeated decapeptides (AKPSYPPTYK: SEQ ID NO: 2) was prepared according to a known process (see Proc. Natl. Acad. Sci. USA 2010, 107, 12850-3). Thereafter, in vitro enzymatic reaction using mushroom tyrosinase (SIGMA) was performed to convert tyrosine residues of the fp-1 variant into dihydroxyphenylalanine (DOPA). Specifically, 1.50 mg/mL of fp-1 variant solution and 100 μg/mL of tyrosinase were reacted in a buffer solution (100 mN of sodium phosphate, 20 mM of boric acid, and 25 mM of ascorbic acid; pH 6.8) for 1 hour, and dialyzed with 1% acetic acid.

Figure 1:
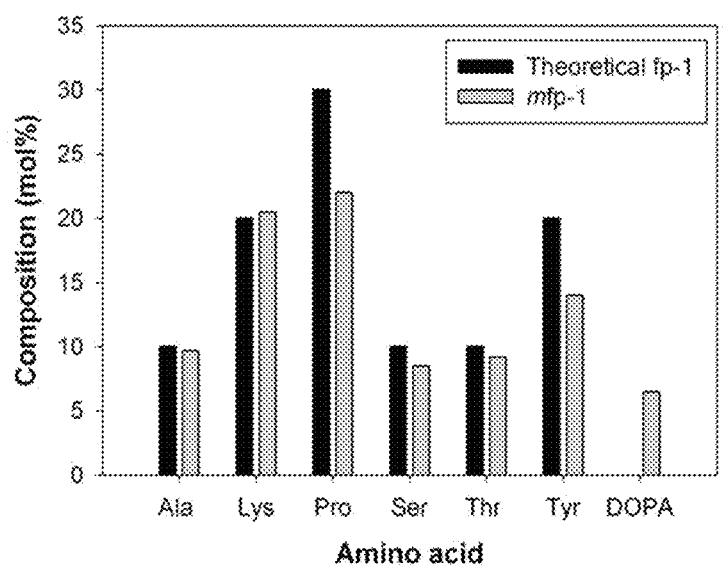
FIG. 1 shows the analysis of amino acid composition for quantifying conversion rate of tyrosine residues of a mussel adhesive protein into DOPA residues.

Thereafter, in order to analyze modification efficiency of the mussel adhesive protein fp-1 variant, the amino acid composition was analyzed. As a result, it was identified that about 30% of the total tyrosine residues were converted into DOPA. The result is shown in FIG. 1.

1.2 Preparation of DOX-Loaded Fe(β)-DOPA Complex Nanoparticles

In order to prepare complex nanoparticles using mfp-1 prepared in Example 1.1 above, electrospraying was used. Specifically, 1.5 to 3 wt % of mfp-1 was dissolved in a solvent including distilled water:ethanol (30:70), and the solvent was electrosprayed. Electrospraying was proceeded to produce nanoparticles by applying a high voltage of 6 to 14 kV when the solution passes through a needle with a diameter of 0.4 mm, while discharging the solution at a flow rate of 1 ml/h using a syringe pump. The prepared nanoparticles were collected into a stirring water bath including phosphate buffered saline (PBS; pH 7.4) or aluminum foil.

Then, in order to prepare Fe(β)-DOPA complex nanoparticles, FeCl₃ solution was added to the mfp-1 solution, such that the molar ratio of Fe:DOPA is 1:3. Then, the mixed solution was electrosprayed. In this case, the prepared nanoparticles were collected directly into a buffer solution (pH 7.4) for spontaneous curing of Fe(β)-DOPA complexes.

Thereafter, in order to prepare doxorubicin (DOX)-loaded Fe(III)-DOPA complex nanoparticles, a DOX solution was added to the FeCl₃-mixed mfp-1 solution, and the mixed solution was electrosprayed directly into PBS. Thereafter, three times dialyses were conducted on PBS (pH 7.4) using molecular weight cut off (MWCO) 3500 membrane to remove unloaded DOX. Thereby, pure DOX-loaded Fe(III)-DOPA complex nanoparticles in purple were obtained.

Experiment Example 1. Analysis on Properties of DOX-Loaded Fe(III)-DOPA Complex Nanoparticles 1.1 Analysis Method DOX loading efficiency was calculated based on the amount of DOX measured from a solution containing unloaded DOX by dialysis and the total amount of initial DOX. Also, in order to analyze the amount of DOX loaded in the complex nanoparticles, a reference curve was obtained using free-state DOX, and then fluorescence intensity was measured with a fluorescence spectrometer (Perkin Elmer, USA) with excitation and emission filter set as 450 nm and 590 nm.

To measure particle size and polydispersity index, dynamic light scattering (DLS; Zetasizer, UK) equipment was used. The concentration of mfp-1 nanoparticles in suspension was 1 mg/mL or less and all measurements were carried out at room temperature.

The morphology of electrosprayed nanoparticles was observed by scanning electron microscopy (SEM; JSM-7401F; JEOL, Japan) and transmission electron microscopy (TEM; JEM-2100F; JEOL). mfp-1 nanoparticles on aluminum foil were analyzed by SEM at an accelerating voltage of 5 and 20 kV after gold sputtering. For TEM analysis, nanoparticles were directly electrosprayed onto copper grids and observed at an accelerating voltage of 200 kV in a vacuum state.

To visualize the co-localization of mfp-1 and DOX in the electrosprayed nanoparticles, fluorescein isothiocyanate (FITC)-conjugated fp-1, instead of mfp-1, was used in the same electrospray process. Thereafter, fluorescence images were obtained using fluorescence microscopy (Olympus, Japan).

1.2 Analysis on Properties of DOX-Loaded Fe(III)-DOPA Complex Nanoparticles

DOX loading efficiency of DOX-loaded mfp-1 complex nanoparticles is shown in Table 1 below.

TABLE 1

| Molar ratio (mfp-1:DOX) | $D_h{}^1$(nm) | PDI[1] | DLE[2](wt %) |
| --- | --- | --- | --- |
| 1:1 | 138.8 | 0.54 | 53.2 |
| 1:2 | 87.8 | 0.24 | 66.6 |
| 1:4 | 81.8 | 0.45 | 75.5 |

[1]Hydrodynamic particle size ($D_h$) and polydispersity index (PDI) of DOX-loaded mfp-1 complex nanoparticles in water determined by DLS
[2]Drug loading efficiency (DLE) calculated based on fluorescence intensity of DOX As shown in Table 1, DOX loading efficiency was calculated as 50 to 75%, and it was found that the loading efficiency varied depending on the mixing molar ratio between mfp-1 and DOX.

FIG. 2(A) to 2(C) each shows SEM morphology, TEM morphology, and particle size distribution by DLS of DOX-loaded mfp-1 complex nanoparticles. FIG. 2(D) shows fluorescence microscopic merged image of electrosprayed DOX-loaded FITC-conjugated fp-1 nanoparticles.

Figure 2:
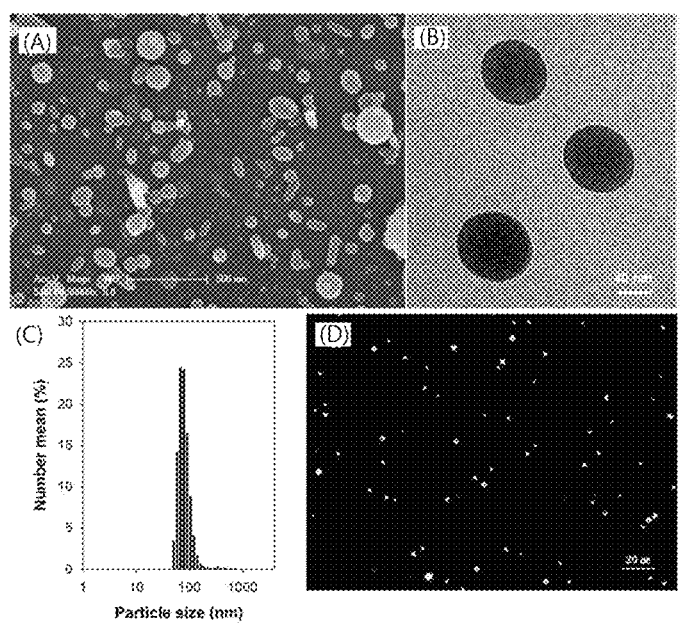
FIG. 2 shows SEM morphology (A), TEM morphology (B), particle size distribution by DLS (C) of doxorubicin (DOX)-loaded mfp-1 nanoparticles, and fluorescence microscopic merged image of electrosprayed DOX-loaded FITC-conjugated fp-1 nanoparticles (D).

As shown in FIG. 2, as a result of DLS analysis, it indicated that DOX-loaded mfp-1 complex nanoparticles have a mean diameter of 80 to 130 nm. Also, as a result of fluorescence microscopic analysis, it was observed that DOX and FITC-conjugated fp-1 are co-located in complex nanoparticles.

Experiment Example 2. Analysis on DOX Release of DOX-Loaded mfp-1 Complex Nanoparticles 2.1 Analysis Method DOX release from mfp-1 complex nanoparticles was evaluated in vitro under different pH environments. 1 mL of solution in PBS containing electrosprayed mfp-1 complex nanoparticles was tubed in the dialysis membrane (MWCO 3500) and incubated in 10 mL of each buffer solution with different pH by shaking at 37° C. At determined time period, 1 mL of each solution was sampled and fresh buffer was replaced. The amount of released DOX was measured by a fluorescence spectrometer. To identify presence of Fe(III)-DOPA complexes in each solution, resulting solutions after release test were collected and absorbance spectrum was analyzed using UV-visible spectrophotometer (Shimadzu, Japan).

2.2 Analysis Result

FIGS. 3(A) and 3(B) illustrate in vitro DOX release profiles and color detection of DOX-loaded mfp-1 complex nanoparticles according to pH. FIG. 3(C) illustrates UV absorbance spectrum of DOX-loaded mfp-1 nanoparticles after release test. Here, arrow indicates representative peaks (around 500 and 540 nm) of tris- and bis-cross-links between Fe(III) and DOPA, respectively.

Figure 3:
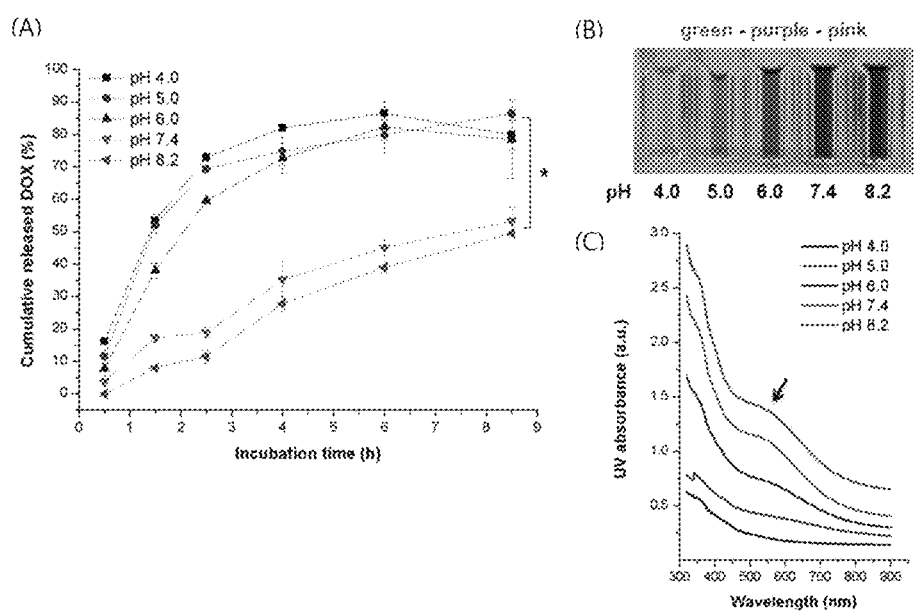
FIG. 3 shows in vitro DOX release profiles (A) and color detection (B) of DOX-loaded mfp-1 nanoparticles according to pH, and UV absorbance spectrum of DOX-loaded mfp-1 nanoparticles after release (C). Here, arrow indicates representative peaks (around 500 and 540 nm) of tris- and bis-cross-links between Fe(III) and DOPA, respectively.

As shown in FIG. 3, it was indicated that DOX release was significantly increased at pH 6 or lower, compared with higher pH buffers, and that about 4-fold or more enhancement of DOX release was detected for initial 3 hours. This result demonstrated strong pH-responsive drug releasing effect of mfp-1 complex nanoparticles. Also, it was observed that initial purple-pink color as well as spectroscopic absorbance at around 500 and 540 nm gradually disappeared through incubating under more acidic pH conditions. This result indicated that the number of coordinations between Fe(III) and DOPA was gradually reduced. The pH-dependent mfp-1 complex nanoparticles have the mechanism that drugs in the polymers with tight packing have a chance to diffuse by pH-induced loosened cross-linking networks.

Experiment Example 3. Evaluation on Cytotoxicity and Cellular Uptake of mfp-1 Nanoparticles 3.1 Analysis Method The following evaluation experiments were carried out based on cell cultures using HeLa cell line (ATCC No. CCL-2). HeLa cells were cultured and maintained in Dulbecco's Modified Eagle's Media (DMEM; Hyclone) supplemented with 10% fetal bovine serum (FBS; Lonza) and 1% penicillin/streptomycin (Hyclone) at 37° C. under a humidified atmosphere of 5% CO2 and 95% air. The confluent cells were detached using 0.25% trypsin-EDTA, and the viable cells counted by a trypan blue assay were used for further analysis. For cytotoxicity evaluation, cells were initially seeded on 24-well culture plate at a density of $5\times10^4$ cells per well, and cultured for 1 day. Free DOX, original mfp-1 nanoparticles, and DOX-loaded mfp-1 nanoparticles with predetermined concentrations were treated into the media and cell viability was measured after 15 hours' incubation. Cell viability was determined by measuring absorbance at 450 nm from aliquots of each medium after treating CCK-8 reagent (Dojindo, Japan) into the culture media and incubating for 2 hours.

For cellular uptake evaluation, cell imaging and flow cytometer analysis were performed. For cell imaging, free DOX and DOX-loaded mfp-1 nanoparticles (DOX concentration 2 μg/mL) were treated for 1 and 3 hours into each cell culture medium after initial cell seeding on 24-well culture plate. Before observation, cells were stained with 5 μg/mL of Hoechst 33258 (Sigma) solution for 30 minutes to clearly discriminate cell nucleus from cytosol. Cell nucleus and location of DOX were observed using fluorescence microscopy (Olympus). Cells treated by same condition with imaging procedures were collected for flow cytometry analysis after detachment by 0.25% trypsin-EDTA treatment. Fluorescence intensity of DOX in the collected cells resuspended in 1 mL PBS was examined by fluorescence scanning with $1\times10^4$ cells under PerCP-Cy5.5 filter (488 nm excitation and 630 nm emission). Calibration was performed using non-treated cells.

3.2 Analysis Result

Figure 4:
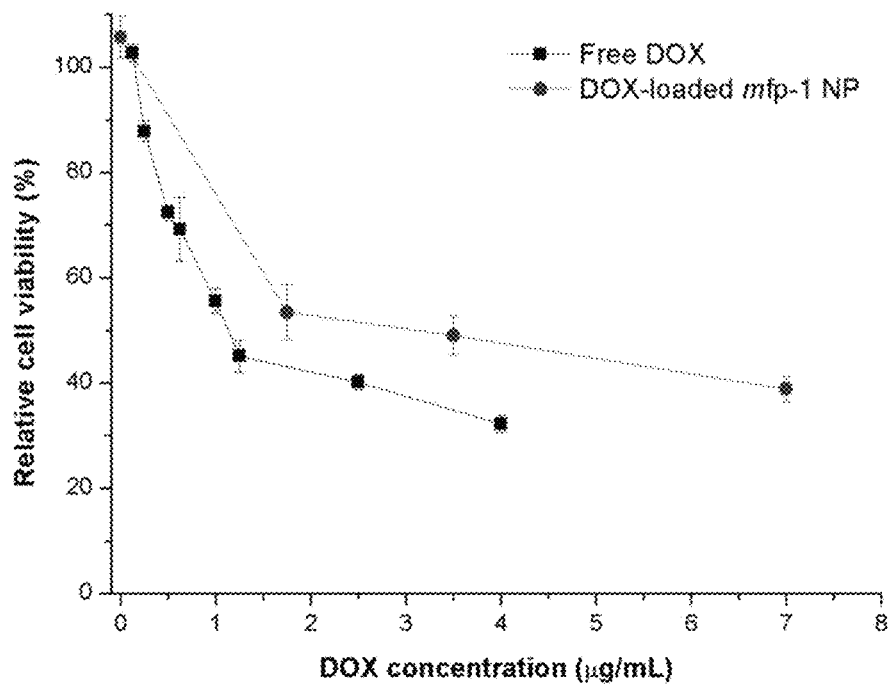
FIG. 4 shows relative HeLa cell viability of DOX-loaded mfp-1 nanoparticles according to DOX concentrations. Here, a value at zero point of DOX concentration indicates the cell viability after treatment of mfp-1 nanoparticles without DOX.

FIG. 4 shows relative HeLa cell viability of DOX-loaded mfp-1 nanoparticles according to DOX concentrations. Here, a value at zero point of DOX concentration indicates the cell viability after treatment of mfp-1 nanoparticles without DOX.

As shown in FIG. 4, it was identified that DOX-loaded mfp-1 showed strong cytotoxicity on cancer cells, whereas mfp-1 containing no DOX showed no cytotoxicity, and that the half maximal inhibitory concentration ($IC_{50}$) was determined as up to 2 μg/mL, of which level is twice higher than that (up to 1 μg/mL) of free DOX as the control group. With the effective cytotoxicity of DOX-loaded mfp-1 nanoparticles, it was believed that acid environment of endosomes actually helps DOX loaded inside mfp-1 nanoparticles being released into the cytosol.

Figure 5:
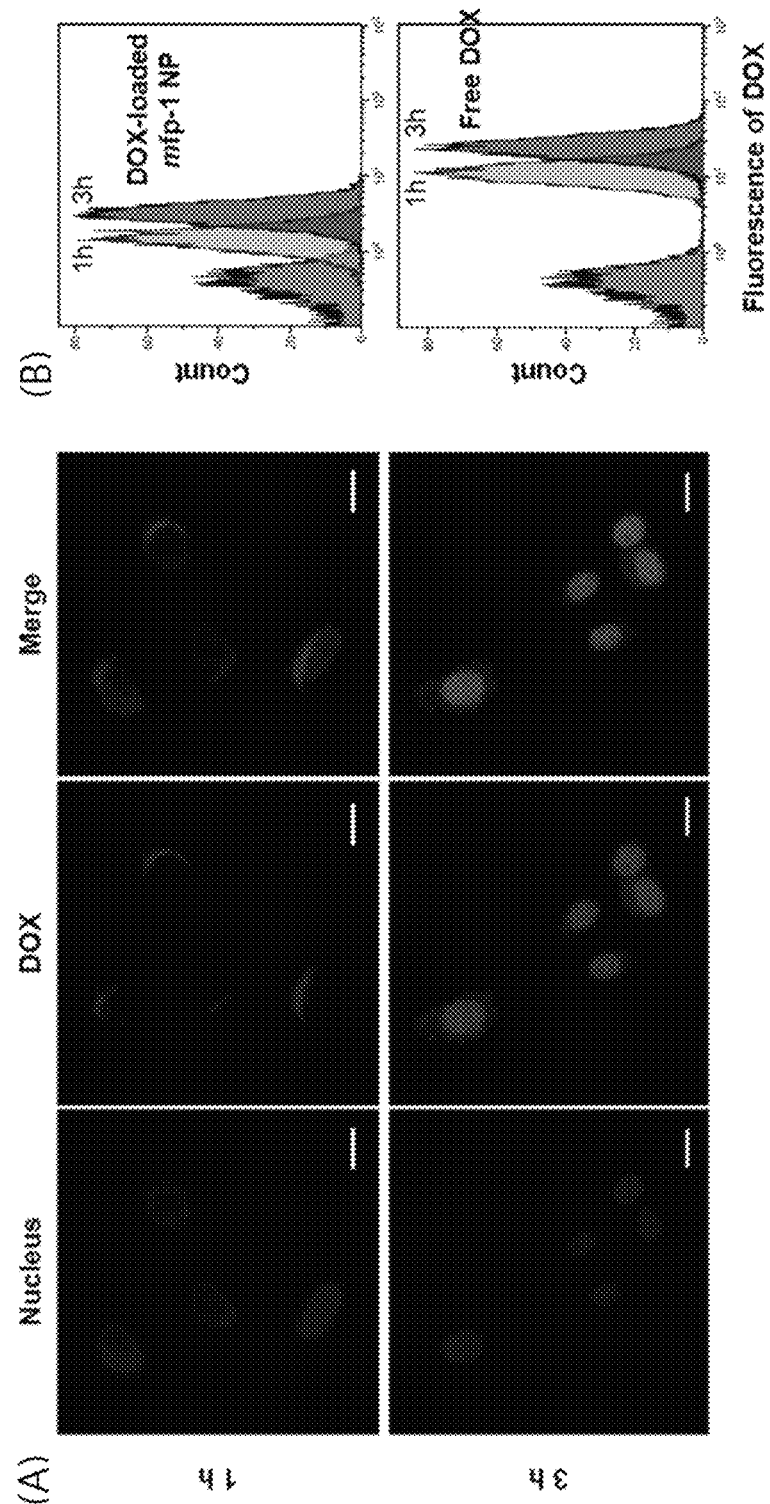
FIG. 5 shows fluorescence microscopic images (A) and flow cytometric analyses (B) of HeLa cells incubated with DOX-loaded mfp-1 nanoparticles for 1 and 3 hours.

FIG. 5 shows fluorescence microscopic images (FIG. 5(A)) and flow cytometric analyses (FIG. 5(B)) of HeLa cells incubated with DOX-loaded mfp-1 nanoparticles for 1 and 3 hours.

As shown in FIG. 5(A), it was observed that DOX-loaded mfp-1 nanoparticles treated for 1 hour was localized near the cell membrane and spread throughout the cytosol including cell nucleus after the treatment of 3 hours. However, it was detected that DOX spread over the whole cell area after the treatment with free DOX for 1 hour.

Also, as shown in FIG. 5(B), in consistent with the imaging analysis results, a strong fluorescence signal was measured in DOX-loaded mfp-1 nanoparticles-treated cells and the intensity was gradually augmented by increased incubation time. Fluorescence intensity in free DOX-treated cells was higher than DOX-loaded mfp-1 nanoparticles-treated cells. Normally, except for extremely small sized nanoparticles (<50 nm), nanoparticles of 500 nm or smaller size are believed to be internalized into the cells through endocytosis.

Figure 6:
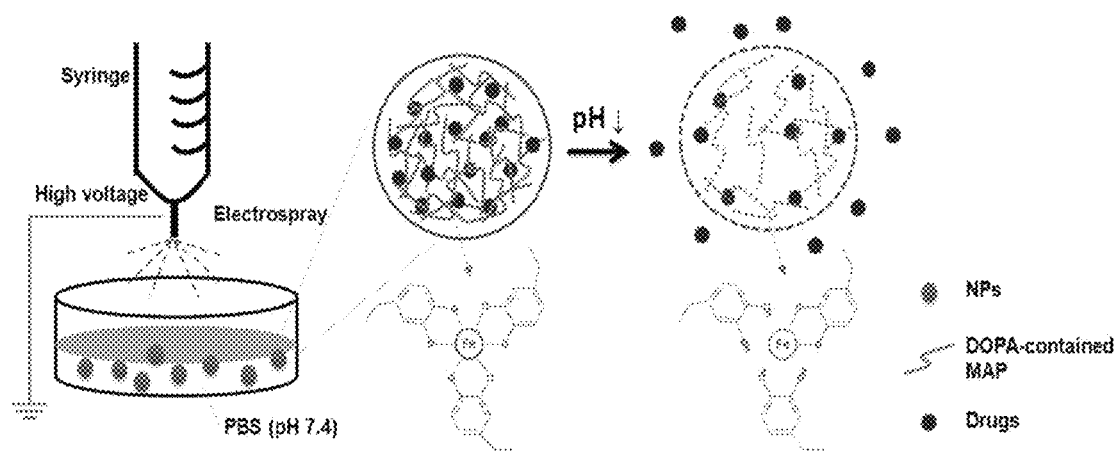
FIG. 6 shows schematic representation of polymeric NP synthesis based on Fe(III)-DOPA complexation with recombinant DOPA-contained MAP using electrospraying process and pH-responsive release of drug.

Taking the above results together, novel drug-loaded nanoparticles were prepared using the mussel adhesive protein and electrospraying, and their cross-links and pH-responsive drug release behaviors were achieved by stoichiometry of Fe(III)-DOPA complexation (FIG. 6). It was found that the prepared Fe(III)-DOPA complex nanoparticles have cytotoxic efficacy on cancer cells through efficient cellular uptakes and their cytosolic release.

What is claimed is:

1. A pH-responsive nanoparticle for drug delivery, comprising:
   a mussel adhesive protein of which a tyrosine residue is converted to 3,4-dihydroxyphenylalanine (DOPA);
   a metal capable of forming a coordinate bond with the DOPA; and
   a drug.

2. The nanoparticle of claim 1, wherein the mussel adhesive protein comprises the amino acid sequence of SEQ ID NO: 3.

3. The nanoparticle of claim 1, wherein 10 to 100% of the tyrosine residues are converted into the DOPA.

4. The nanoparticle of claim 1, wherein the metal capable of forming a coordinate bond with the DOPA is at least one selected from the group consisting of titanium, vanadium, chrome, manganese, iron, cobalt, nickel, zirconium, niobium, molybdenum, technetium, ruthenium, rhodium, palladium, silver, hafnium, tantalum, tungsten, rhenium, osmium, iridium, platinum, and gold.

5. The nanoparticle of claim 1, wherein the DOPA and the metal form a coordinate bond to obtain a metal DOPA complex.

6. The nanoparticle of claim 5, wherein the metal DOPA complex is a Fe(III)-DOPA complex.

7. The nanoparticle of claim 1, wherein the drug is a low molecular weight drug, a genetic drug, a protein drug, an antibody drug, a synthetic compound drug, or a combination thereof.

8. The nanoparticle of claim 7, wherein the molecular weight drug is at least one selected from the group consisting of doxorubicin, dactinomycin, mitomycin, bleomycin, cytarabine, azaserine, cyclophosphamide, triethylenemelamine, treosulfan, retinoic acid, vinblastine, vincristine, aspirin, salicylate, ibuprofen, flurbiprofen, piroxicam, naproxen, fenoprofen, indomethacin, phenylbutazone, methotrexate, mechlorethamine, dexamethasone, prednisolone, celecoxib, valdecoxib, nimesulide, cortisone, and corticosteroid.

9. The nanoparticle of claim 1, wherein the drug is at least one anti-cancer drug selected from the group consisting of doxorubicin, paclitaxel, docetaxel, cisplatin, carboplatin, 5-FU, etoposide, and camptothecin.

10. The nanoparticle of claim 1, wherein the nanoparticle is capable of releasing a drug at pH 0.1 to 6.5.

11. The nanoparticle of claim 1, wherein the nanoparticle has a mean diameter of 80 to 130 nm.

12. The nanoparticle of claim 1, wherein the nanoparticle is used for at least one cancer selected from the group consisting of skin cancer, melanoma, stomach cancer, esophageal cancer, colon cancer, pancreatic cancer, colorectal cancer, rectal cancer, cholangiocarcinoma, liver cancer, brain tumor, leukemia, osteosarcoma, bone cancer, breast cancer, thyroid cancer, lung adenocarcinoma, uterine cancer, uterine cervix cancer, endometrial cancer, head and neck cancer, endocrine adenocarcinoma, urethra cancer, ovarian cancer, testis cancer, kidney cancer, bladder cancer, prostate cancer, and lymphoma.

13. An anti-cancer drug comprising the pH-responsive nanoparticle for drug delivery of claim 1.

14. A method for preparing a pH-responsive nanoparticle for drug delivery, the method comprising:
  (1) mixing a mussel adhesive protein of which a tyrosine residue is converted to DOPA and a metal capable of forming a coordinate bond with the DOPA; and
  (2) mixing a drug with the mixture, followed by electrospraying.

15. The method of claim 14, wherein the mussel adhesive protein and the drug are mixed in a mixing ratio of 1:0.1 to 1:10 (w/w).

16. The method of claim 14, wherein a solvent used for the electrospraying is a mixed solvent of distilled water and an organic solvent.

* * * * *

SEQUENCE LISTING

<160> NUMBER OF SEQ ID NOS: 25

<210> SEQ ID NO 1
<211> LENGTH: 565
<212> TYPE: PRT
<213> ORGANISM: Artificial Sequence
<220> FEATURE:
<223> OTHER INFORMATION: fp-1

<400> SEQUENCE: 1

```
Met Glu Gly Ile Lys Leu Asn Leu Cys Leu Leu Cys Ile Phe Thr Phe
 1               5                  10                  15

Asp Val Leu Gly Phe Ser Asn Gly Asn Ile Tyr Asn Ala His Val Ser
            20                  25                  30

Ser Tyr Ala Gly Ala Ser Ala Gly Ala Tyr Lys Lys Leu Pro Asn Ala
        35                  40                  45

Tyr Pro Tyr Gly Thr Lys Pro Glu Pro Val Tyr Lys Pro Val Lys Thr
    50                  55                  60

Ser Tyr Ser Ala Pro Tyr Lys Pro Pro Thr Tyr Gln Gln Leu Lys Lys
65                  70                  75                  80

Lys Val Asp Tyr Arg Pro Thr Lys Ser Tyr Pro Pro Thr Tyr Gly Ser
                85                  90                  95

Lys Thr Asn Tyr Leu Pro Leu Ala Lys Lys Leu Ser Ser Tyr Lys Pro
            100                 105                 110

Ile Lys Thr Thr Tyr Asn Ala Lys Thr Asn Tyr Pro Pro Val Tyr Lys
        115                 120                 125

Pro Lys Met Thr Tyr Pro Thr Tyr Lys Pro Lys Pro Ser Tyr Pro
    130                 135                 140

Pro Thr Tyr Lys Ser Lys Pro Thr Tyr Pro Lys Ile Thr Cys Pro
145                 150                 155                 160

Pro Thr Tyr Lys Ala Lys Pro Ser Tyr Pro Thr Tyr Lys Pro Lys
                165                 170                 175

Lys Thr Tyr Pro Pro Thr Tyr Lys Pro Lys Val Thr Tyr Pro Pro Thr
            180                 185                 190

Tyr Lys Pro Lys Pro Ser Tyr Pro Pro Ile Tyr Lys Ser Lys Pro Thr
        195                 200                 205

Tyr Lys Pro Lys Ile Thr Tyr Pro Pro Thr Tyr Lys Ala Lys Pro Ser
    210                 215                 220

Tyr Pro Pro Thr Tyr Lys Ala Lys Pro Ser Tyr Pro Pro Thr Tyr Lys
225                 230                 235                 240

Ala Lys Pro Thr Tyr Lys Ala Lys Pro Thr Tyr Pro Ser Thr Tyr Lys
                245                 250                 255

Ala Lys Pro Thr Tyr Pro Pro Thr Tyr Lys Ala Lys Pro Ser Tyr Pro
            260                 265                 270

Pro Thr Tyr Lys Ala Lys Pro Ser Tyr Pro Pro Thr Tyr Lys Ala Lys
        275                 280                 285

Pro Thr Tyr Ile Ala Lys Pro Ser Tyr Pro Pro Thr Tyr Lys Ala Lys
    290                 295                 300

Pro Ser Tyr Pro Pro Thr Tyr Lys Ala Lys Pro Ser Tyr Pro Pro Thr
305                 310                 315                 320

Tyr Lys Ala Lys Ser Ser Tyr Pro Pro Thr Tyr Lys Ala Lys Pro Thr
                325                 330                 335

Tyr Lys Ala Lys Pro Thr Tyr Pro Ser Thr Tyr Lys Ala Lys Pro Ser
            340                 345                 350

Tyr Pro Pro Thr Tyr Lys Ala Lys Pro Thr Tyr Lys Ala Lys Pro Thr
```

```
                355                 360                 365
Tyr Pro Ser Thr Tyr Lys Ala Lys Pro Thr Tyr Pro Ser Thr Tyr Lys
    370                 375                 380

Ala Lys Pro Ser Tyr Pro Pro Thr Tyr Lys Pro Lys Ile Ser Tyr Pro
385                 390                 395                 400

Pro Thr Tyr Lys Ala Lys Pro Ser Tyr Pro Ser Thr Tyr Lys Ala Lys
                405                 410                 415

Ser Ser Tyr Pro Pro Thr Tyr Lys Ala Lys Pro Ser Tyr Pro Pro Thr
                420                 425                 430

Tyr Lys Ala Lys Pro Thr Tyr Lys Ala Lys Pro Thr Tyr Pro Ser Thr
            435                 440                 445

Tyr Lys Ala Lys Pro Thr Tyr Lys Ala Lys Pro Thr Tyr Pro Pro Thr
        450                 455                 460

Tyr Lys Ala Lys Pro Ser Tyr Pro Pro Thr Tyr Lys Pro Lys Pro Ser
465                 470                 475                 480

Tyr Pro Pro Thr Tyr Lys Ser Lys Ser Ser Tyr Pro Ser Ser Tyr Lys
                485                 490                 495

Pro Lys Lys Thr Tyr Pro Pro Thr Tyr Lys Pro Lys Leu Thr Tyr Pro
                500                 505                 510

Pro Thr Tyr Lys Pro Lys Pro Ser Tyr Pro Ser Tyr Lys Pro Lys
            515                 520                 525

Ile Thr Tyr Pro Ser Thr Tyr Lys Leu Lys Pro Ser Tyr Pro Pro Thr
        530                 535                 540

Tyr Lys Ser Lys Thr Ser Tyr Pro Pro Thr Tyr Asn Lys Lys Ile Ser
545                 550                 555                 560

Tyr Pro Ser Gln Tyr
                565

<210> SEQ ID NO 2
<211> LENGTH: 10
<212> TYPE: PRT
<213> ORGANISM: Artificial Sequence
<220> FEATURE:
<223> OTHER INFORMATION: fragment sequence derived from fp-1

<400> SEQUENCE: 2

Ala Lys Pro Ser Tyr Pro Pro Thr Tyr Lys
1               5                   10

<210> SEQ ID NO 3
<211> LENGTH: 120
<212> TYPE: PRT
<213> ORGANISM: Artificial Sequence
<220> FEATURE:
<223> OTHER INFORMATION: fp-1 variant

<400> SEQUENCE: 3

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ala Lys Pro Ser
        50                  55                  60

Tyr Pro Pro Thr Tyr Lys Ala Lys Pro Ser Tyr Pro Pro Thr Tyr Lys
65                  70                  75                  80
```

```
Ala Lys Pro Ser Tyr Pro Pro Thr Tyr Lys Ala Lys Pro Ser Tyr Pro
                85                  90                  95

Pro Thr Tyr Lys Ala Lys Pro Ser Tyr Pro Pro Thr Tyr Lys Ala Lys
            100                 105                 110

Pro Ser Tyr Pro Pro Thr Tyr Lys
        115                 120

<210> SEQ ID NO 4
<211> LENGTH: 126
<212> TYPE: PRT
<213> ORGANISM: Artificial Sequence
<220> FEATURE:
<223> OTHER INFORMATION: fp-1 variant-RGD

<400> SEQUENCE: 4

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ala Lys Pro Ser
    50                  55                  60

Tyr Pro Pro Thr Tyr Lys Ala Lys Pro Ser Tyr Pro Pro Thr Tyr Lys
65                  70                  75                  80

Ala Lys Pro Ser Tyr Pro Pro Thr Tyr Lys Ala Lys Pro Ser Tyr Pro
                85                  90                  95

Pro Thr Tyr Lys Ala Lys Pro Ser Tyr Pro Pro Thr Tyr Lys Ala Lys
            100                 105                 110

Pro Ser Tyr Pro Pro Thr Tyr Lys Gly Arg Gly Asp Ser Pro
        115                 120                 125

<210> SEQ ID NO 5
<211> LENGTH: 456
<212> TYPE: PRT
<213> ORGANISM: Artificial Sequence
<220> FEATURE:
<223> OTHER INFORMATION: fp-2

<400> SEQUENCE: 5

Thr Asn Arg Pro Asp Tyr Asn Asp Asp Glu Glu Asp Tyr Lys Pro
1               5                   10                  15

Pro Val Tyr Lys Pro Ser Pro Ser Lys Tyr Arg Pro Val Asn Pro Cys
            20                  25                  30

Leu Lys Lys Pro Cys Lys Tyr Asn Gly Val Cys Lys Pro Arg Gly Gly
            35                  40                  45

Ser Tyr Lys Cys Phe Cys Lys Gly Gly Tyr Tyr Gly Tyr Asn Cys Asn
    50                  55                  60

Leu Lys Asn Ala Cys Lys Pro Asn Gln Cys Lys Asn Lys Ser Arg Cys
65                  70                  75                  80

Val Pro Val Gly Lys Thr Phe Lys Cys Val Cys Arg Asn Gly Asn Phe
                85                  90                  95

Gly Arg Leu Cys Glu Lys Asn Val Cys Ser Pro Asn Pro Cys Lys Asn
            100                 105                 110

Asn Gly Lys Cys Ser Pro Leu Gly Lys Thr Gly Tyr Lys Cys Thr Cys
            115                 120                 125

Ser Gly Gly Tyr Thr Gly Pro Arg Cys Glu Val His Ala Cys Lys Pro
        130                 135                 140
```

Asn Pro Cys Lys Asn Lys Gly Arg Cys Phe Pro Asp Gly Lys Thr Gly
145                 150                 155                 160

Tyr Lys Cys Arg Cys Val Asp Gly Tyr Ser Gly Pro Thr Cys Gln Glu
            165                 170                 175

Asn Ala Cys Lys Pro Asn Pro Cys Ser Asn Gly Gly Thr Cys Ser Ala
        180                 185                 190

Asp Lys Phe Gly Asp Tyr Ser Cys Glu Cys Arg Pro Gly Tyr Phe Gly
    195                 200                 205

Pro Glu Cys Glu Arg Tyr Val Cys Ala Pro Asn Pro Cys Lys Asn Gly
210                 215                 220

Gly Ile Cys Ser Ser Asp Gly Ser Gly Tyr Arg Cys Arg Cys Lys
225                 230                 235                 240

Gly Gly Tyr Ser Gly Pro Thr Cys Lys Val Asn Val Cys Lys Pro Thr
                245                 250                 255

Pro Cys Lys Asn Ser Gly Arg Cys Val Asn Lys Gly Ser Ser Tyr Asn
            260                 265                 270

Cys Ile Cys Lys Gly Gly Tyr Ser Gly Pro Thr Cys Gly Glu Asn Val
        275                 280                 285

Cys Lys Pro Asn Pro Cys Gln Asn Arg Gly Arg Cys Tyr Pro Asp Asn
    290                 295                 300

Ser Asp Gly Phe Lys Cys Arg Cys Val Gly Gly Tyr Lys Gly Pro
305                 310                 315                 320

Thr Cys Glu Asp Lys Pro Asn Pro Cys Asn Thr Lys Pro Cys Lys Asn
                325                 330                 335

Gly Gly Lys Cys Asn Tyr Asn Gly Lys Ile Tyr Thr Cys Lys Cys Ala
            340                 345                 350

Tyr Gly Trp Arg Gly Arg His Cys Thr Asp Lys Ala Tyr Lys Pro Asn
        355                 360                 365

Pro Cys Val Val Ser Lys Pro Cys Lys Asn Arg Gly Lys Cys Ile Trp
    370                 375                 380

Asn Gly Lys Ala Tyr Arg Cys Lys Cys Ala Tyr Gly Tyr Gly Gly Arg
385                 390                 395                 400

His Cys Thr Lys Lys Ser Tyr Lys Asn Pro Cys Ala Ser Arg Pro
                405                 410                 415

Cys Lys Asn Arg Gly Lys Cys Thr Asp Lys Gly Asn Gly Tyr Val Cys
            420                 425                 430

Lys Cys Ala Arg Gly Tyr Ser Gly Arg Tyr Cys Ser Leu Lys Ser Pro
        435                 440                 445

Pro Ser Tyr Asp Asp Asp Glu Tyr
    450                 455

<210> SEQ ID NO 6
<211> LENGTH: 46
<212> TYPE: PRT
<213> ORGANISM: Artificial Sequence
<220> FEATURE:
<223> OTHER INFORMATION: fp-3

<400> SEQUENCE: 6

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

```
<210> SEQ ID NO 7
<211> LENGTH: 787
<212> TYPE: PRT
<213> ORGANISM: Artificial Sequence
<220> FEATURE:
<223> OTHER INFORMATION: fp-4

<400> SEQUENCE: 7

Tyr Gly Arg Arg Tyr Gly Glu Pro Ser Gly Tyr Ala Asn Ile Gly His
 1               5                  10                  15

Arg Arg Tyr Tyr Glu Arg Ala Ile Ser Phe His Arg His Ser His Val
             20                  25                  30

His Gly His His Leu Leu His Arg His Val His Arg His Ser Val Leu
         35                  40                  45

His Gly His Val His Met His Arg Val Ser His Arg Ile Met His Arg
     50                  55                  60

His Arg Val Leu His Gly His Val His Arg His Arg Val Leu His Arg
 65                  70                  75                  80

His Val His Arg His Arg Val Leu His Gly His Val His Arg His Arg
                 85                  90                  95

Val Leu His Arg His Leu His Arg His Arg Val Leu His Gly His Val
            100                 105                 110

His Arg His Arg Val Leu His Asn His Val His Arg His Ser Val Leu
        115                 120                 125

His Gly His Val His Arg His Arg Val Leu His Arg His Val His Arg
    130                 135                 140

His Asn Val Leu His Gly His Val His Arg His Arg Val Leu His Lys
145                 150                 155                 160

His Val His Asp His Arg Val Leu His Lys His Leu His Lys His Gln
                165                 170                 175

Val Leu His Gly His Val His Arg His Gln Val Leu His Lys His Val
            180                 185                 190

His Asn His Arg Val Leu His Lys His Leu His Lys His Gln Val Leu
        195                 200                 205

His Gly His Val His Thr His Arg Val Leu His Lys His Val His Lys
    210                 215                 220

His Arg Val Leu His Lys His Leu His Lys His Gln Val Leu His Gly
225                 230                 235                 240

His Ile His Thr His Arg Val Leu His Lys His Leu His Lys His Gln
                245                 250                 255

Val Leu His Gly His Val His Thr His Arg Val Leu His Lys His Val
            260                 265                 270

His Lys His Arg Val Leu His Lys His Leu His Lys His Gln Val Leu
        275                 280                 285

His Gly His Val His Met His Arg Val Leu His Lys His Val His Lys
    290                 295                 300

His Arg Val Leu His Lys His Val Lys His His Val Val His Lys
305                 310                 315                 320

His Val His Ser His Arg Val Leu His Lys His Val His Lys His Arg
                325                 330                 335

Val Glu His Gln His Val His Lys His Val Leu His Arg His Val
            340                 345                 350

His Ser His His Val Val His Ser His Val His Lys His Arg Val Val
        355                 360                 365
```

```
His Ser His Val His Lys His Asn Val Val His Ser His Val His Arg
    370                 375                 380
His Gln Ile Leu His Arg His Val His Arg His Gln Val Val His Arg
385                 390                 395                 400
His Val His Arg His Leu Ile Ala His Arg His Ile His Ser His Gln
                405                 410                 415
Ala Ala Val His Arg His Val His Thr His Val Phe Glu Gly Asn Phe
            420                 425                 430
Asn Asp Asp Gly Thr Asp Val Asn Leu Arg Ile Arg His Gly Ile Ile
        435                 440                 445
Tyr Gly Gly Asn Thr Tyr Arg Leu Ser Gly Gly Arg Arg Arg Phe Met
    450                 455                 460
Thr Leu Trp Gln Glu Cys Leu Glu Ser Tyr Gly Asp Ser Asp Glu Cys
465                 470                 475                 480
Phe Val Gln Leu Gly Asn Gln His Leu Phe Thr Val Val Gln Gly His
                485                 490                 495
His Ser Thr Ser Phe Arg Ser Asp Leu Ser Asn Asp Leu His Pro Asp
            500                 505                 510
Asn Asn Ile Glu Gln Ile Ala Asn Asp His Val Asn Asp Ile Ala Gln
        515                 520                 525
Ser Thr Asp Gly Asp Ile Asn Asp Phe Ala Asp Thr His Tyr Asn Asp
    530                 535                 540
Val Ala Pro Ile Ala Asp Val His Val Asp Asn Ile Ala Gln Thr Ala
545                 550                 555                 560
Asp Asn His Val Lys Asn Ile Ala Gln Thr Ala His His Val Asn
                565                 570                 575
Asp Val Ala Gln Ile Ala Asp Asp His Val Asn Asp Ile Gly Gln Thr
            580                 585                 590
Ala Tyr Asp His Val Asn Asn Ile Gly Gln Thr Ala Asp Asp His Val
        595                 600                 605
Asn Asp Ile Ala Gln Thr Ala Asp Asp His Val Asn Ala Ile Ala Gln
    610                 615                 620
Thr Ala Asp Asp His Val Asn Ala Ile Ala Gln Thr Ala Asp His Val
625                 630                 635                 640
Asn Asp Ile Gly Asp Thr Ala Asn Ser His Ile Val Arg Val Gln Gly
                645                 650                 655
Val Ala Lys Asn His Leu Tyr Gly Ile Asn Lys Ala Ile Gly Lys His
            660                 665                 670
Ile Gln His Leu Lys Asp Val Ser Asn Arg His Ile Glu Lys Leu Asn
        675                 680                 685
Asn His Ala Thr Lys Asn Leu Leu Gln Ser Ala Leu Gln His Lys Gln
    690                 695                 700
Gln Thr Ile Glu Arg Glu Ile Gln His Lys Arg His Leu Ser Glu Lys
705                 710                 715                 720
Glu Asp Ile Asn Leu Gln His Glu Asn Ala Met Lys Ser Lys Val Ser
                725                 730                 735
Tyr Asp Gly Pro Val Phe Asn Glu Lys Val Ser Val Ser Asn Gln
            740                 745                 750
Gly Ser Tyr Asn Glu Lys Val Pro Val Leu Ser Asn Gly Gly Tyr
        755                 760                 765
Asn Gly Lys Val Ser Ala Leu Ser Asp Gln Gly Ser Tyr Asn Glu Gly
    770                 775                 780
```

-continued

Tyr Ala Tyr
785

<210> SEQ ID NO 8
<211> LENGTH: 76
<212> TYPE: PRT
<213> ORGANISM: Artificial Sequence
<220> FEATURE:
<223> OTHER INFORMATION: fp-5

<400> SEQUENCE: 8

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Tyr Tyr Lys Tyr Lys
        35                  40                  45

Asn Ser Gly Lys Tyr Lys Tyr Leu Lys Ala Arg Lys Tyr His Arg
    50                  55                  60

Lys Gly Tyr Lys Lys Tyr Tyr Gly Gly Ser Ser
65                  70                  75

<210> SEQ ID NO 9
<211> LENGTH: 99
<212> TYPE: PRT
<213> ORGANISM: Artificial Sequence
<220> FEATURE:
<223> OTHER INFORMATION: fp-6

<400> SEQUENCE: 9

Gly Gly Gly Asn Tyr Arg Gly Tyr Cys Ser Asn Lys Gly Cys Arg Ser
1               5                   10                  15

Gly Tyr Ile Phe Tyr Asp Asn Arg Gly Phe Cys Lys Tyr Gly Ser Ser
            20                  25                  30

Ser Tyr Lys Tyr Asp Cys Gly Asn Tyr Ala Gly Cys Cys Leu Pro Arg
        35                  40                  45

Asn Pro Tyr Gly Arg Val Lys Tyr Tyr Cys Thr Lys Lys Tyr Ser Cys
    50                  55                  60

Pro Asp Asp Phe Tyr Tyr Tyr Asn Asn Lys Gly Tyr Tyr Tyr Tyr Asn
65                  70                  75                  80

Asp Lys Asp Tyr Phe Asn Cys Gly Ser Tyr Asn Gly Cys Cys Leu Arg
                85                  90                  95

Ser Gly Tyr

<210> SEQ ID NO 10
<211> LENGTH: 196
<212> TYPE: PRT
<213> ORGANISM: Artificial Sequence
<220> FEATURE:
<223> OTHER INFORMATION: fp-151

<400> SEQUENCE: 10

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
            85                  90                  95

Tyr Tyr Gly Lys Ala Lys Lys Tyr Tyr Tyr Lys Tyr Lys Asn Ser Gly
            100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys
            195

<210> SEQ ID NO 11
<211> LENGTH: 202
<212> TYPE: PRT
<213> ORGANISM: Artificial Sequence
<220> FEATURE:
<223> OTHER INFORMATION: fp-151-RGD

<400> SEQUENCE: 11

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
            35                  40                  45

Thr Tyr Lys Ala Lys Pro Ser Tyr Pro Pro Thr Tyr Lys Ser Ser Glu
            50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
            85                  90                  95

Tyr Tyr Gly Lys Ala Lys Lys Tyr Tyr Tyr Lys Tyr Lys Asn Ser Gly
            100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys Gly Arg Gly Asp Ser Pro
            195                 200

<210> SEQ ID NO 12

```
<211> LENGTH: 172
<212> TYPE: PRT
<213> ORGANISM: Artificial Sequence
<220> FEATURE:
<223> OTHER INFORMATION: fp-131

<400> SEQUENCE: 12

Met Ala Lys Pro Ser Tyr Pro Pro Thr Tyr Lys Ala Lys Pro Ser Tyr
 1               5                  10                  15
Pro Pro Thr Tyr Lys Ala Lys Pro Ser Tyr Pro Pro Thr Tyr Lys Ala
                20                  25                  30
Lys Pro Ser Tyr Pro Pro Thr Tyr Lys Ala Lys Pro Ser Tyr Pro Pro
            35                  40                  45
Thr Tyr Lys Ala Lys Pro Ser Tyr Pro Pro Thr Tyr Lys Pro Trp Ala
 50                  55                  60
Asp Tyr Tyr Gly Pro Lys Tyr Gly Pro Pro Arg Arg Tyr Gly Gly Gly
 65                  70                  75                  80
Asn Tyr Asn Arg Tyr Gly Arg Arg Tyr Gly Gly Tyr Lys Gly Trp Asn
                85                  90                  95
Asn Gly Trp Lys Arg Gly Arg Trp Gly Arg Lys Tyr Tyr Gly Ser Ala
            100                 105                 110
Lys Pro Ser Tyr Pro Pro Thr Tyr Lys Ala Lys Pro Ser Tyr Pro Pro
        115                 120                 125
Thr Tyr Lys Ala Lys Pro Ser Tyr Pro Pro Thr Tyr Lys Ala Lys Pro
130                 135                 140
Ser Tyr Pro Pro Thr Tyr Lys Ala Lys Pro Ser Tyr Pro Pro Thr Tyr
145                 150                 155                 160
Lys Ala Lys Pro Ser Tyr Pro Pro Thr Tyr Lys Leu
                165                 170

<210> SEQ ID NO 13
<211> LENGTH: 175
<212> TYPE: PRT
<213> ORGANISM: Artificial Sequence
<220> FEATURE:
<223> OTHER INFORMATION: fp-353

<400> SEQUENCE: 13

Met Ala Asp Tyr Tyr Gly Pro Lys Tyr Gly Pro Pro Arg Arg Tyr Gly
 1               5                  10                  15
Gly Gly Asn Tyr Asn Arg Tyr Gly Arg Arg Tyr Gly Gly Tyr Lys Gly
                20                  25                  30
Trp Asn Asn Gly Trp Lys Arg Gly Arg Trp Gly Arg Lys Tyr Tyr Glu
            35                  40                  45
Phe Ser Ser Glu Glu Tyr Lys Gly Gly Tyr Tyr Pro Gly Asn Ser Asn
 50                  55                  60
His Tyr His Ser Gly Gly Ser Tyr His Gly Ser Gly Tyr His Gly Gly
 65                  70                  75                  80
Tyr Lys Gly Lys Tyr Tyr Gly Lys Ala Lys Tyr Tyr Tyr Lys Tyr
                85                  90                  95
Lys Asn Ser Gly Lys Tyr Lys Tyr Leu Lys Lys Ala Arg Lys Tyr His
            100                 105                 110
Arg Lys Gly Tyr Lys Lys Tyr Tyr Gly Gly Gly Ser Ser Lys Leu Ala
        115                 120                 125
Asp Tyr Tyr Gly Pro Lys Tyr Gly Pro Pro Arg Arg Tyr Gly Gly Gly
130                 135                 140
Asn Tyr Asn Arg Tyr Gly Arg Arg Tyr Gly Gly Tyr Lys Gly Trp Asn
```

```
                  145                 150                 155                 160
Asn Gly Trp Lys Arg Gly Arg Trp Gly Arg Lys Tyr Tyr Leu Glu
            165                 170                 175

<210> SEQ ID NO 14
<211> LENGTH: 189
<212> TYPE: PRT
<213> ORGANISM: Artificial Sequence
<220> FEATURE:
<223> OTHER INFORMATION: fp-153

<400> SEQUENCE: 14

Met Ala Lys Pro Ser Tyr Pro Pro Thr Tyr Lys Ala Lys Pro Ser Tyr
  1               5                  10                  15

Pro Pro Thr Tyr Lys Ala Lys Pro Ser Tyr Pro Pro Thr Tyr Lys Ala
             20                  25                  30

Lys Pro Ser Tyr Pro Pro Thr Tyr Lys Ala Lys Pro Ser Tyr Pro Pro
         35                  40                  45

Thr Tyr Lys Ala Lys Pro Ser Tyr Pro Pro Thr Tyr Lys Glu Phe Ser
     50                  55                  60

Ser Glu Glu Tyr Lys Gly Gly Tyr Tyr Pro Gly Asn Ser Asn His Tyr
 65                  70                  75                  80

His Ser Gly Gly Ser Tyr His Gly Ser Gly Tyr His Gly Gly Tyr Lys
                 85                  90                  95

Gly Lys Tyr Tyr Gly Lys Ala Lys Tyr Tyr Lys Tyr Tyr Lys Lys Asn
            100                 105                 110

Ser Gly Lys Tyr Lys Tyr Leu Lys Lys Ala Arg Lys Tyr His Arg Lys
        115                 120                 125

Gly Tyr Lys Lys Tyr Tyr Gly Gly Ser Ser Lys Leu Ala Asp Tyr
    130                 135                 140

Tyr Gly Pro Lys Tyr Gly Pro Pro Arg Arg Tyr Gly Gly Gly Asn Tyr
145                 150                 155                 160

Asn Arg Tyr Gly Arg Arg Tyr Gly Gly Tyr Lys Gly Trp Asn Asn Gly
                165                 170                 175

Trp Lys Arg Gly Arg Trp Gly Arg Lys Tyr Tyr Leu Glu
            180                 185

<210> SEQ ID NO 15
<211> LENGTH: 189
<212> TYPE: PRT
<213> ORGANISM: Artificial Sequence
<220> FEATURE:
<223> OTHER INFORMATION: fp-351

<400> SEQUENCE: 15

Met Ala Asp Tyr Tyr Gly Pro Lys Tyr Gly Pro Pro Arg Arg Tyr Gly
  1               5                  10                  15

Gly Gly Asn Tyr Asn Arg Tyr Gly Arg Arg Tyr Gly Gly Tyr Lys Gly
             20                  25                  30

Trp Asn Asn Gly Trp Lys Arg Gly Arg Trp Gly Arg Lys Tyr Tyr Glu
         35                  40                  45

Phe Ser Ser Glu Glu Tyr Lys Gly Gly Tyr Tyr Pro Gly Asn Ser Asn
     50                  55                  60

His Tyr His Ser Gly Gly Ser Tyr His Gly Ser Gly Tyr His Gly Gly
 65                  70                  75                  80

Tyr Lys Gly Lys Tyr Tyr Gly Lys Ala Lys Lys Tyr Tyr Lys Tyr
                 85                  90                  95
```

Lys Asn Ser Gly Lys Tyr Lys Tyr Leu Lys Lys Ala Arg Lys Tyr His
            100                 105                 110

Arg Lys Gly Tyr Lys Lys Tyr Tyr Gly Gly Ser Ser Lys Leu Ala
        115                 120                 125

Lys Pro Ser Tyr Pro Pro Thr Tyr Lys Ala Lys Pro Ser Tyr Pro Pro
    130                 135                 140

Thr Tyr Lys Ala Lys Pro Ser Tyr Pro Pro Thr Tyr Lys Ala Lys Pro
145                 150                 155                 160

Ser Tyr Pro Pro Thr Tyr Lys Ala Lys Pro Ser Tyr Pro Pro Thr Tyr
                165                 170                 175

Lys Ala Lys Pro Ser Tyr Pro Pro Thr Tyr Lys Leu Glu
            180                 185

<210> SEQ ID NO 16
<211> LENGTH: 3
<212> TYPE: PRT
<213> ORGANISM: Artificial Sequence
<220> FEATURE:
<223> OTHER INFORMATION: RGD Group 1

<400> SEQUENCE: 16

Arg Gly Asp
 1

<210> SEQ ID NO 17
<211> LENGTH: 4
<212> TYPE: PRT
<213> ORGANISM: Artificial Sequence
<220> FEATURE:
<223> OTHER INFORMATION: RGD Group 2

<400> SEQUENCE: 17

Arg Gly Asp Ser
 1

<210> SEQ ID NO 18
<211> LENGTH: 4
<212> TYPE: PRT
<213> ORGANISM: Artificial Sequence
<220> FEATURE:
<223> OTHER INFORMATION: RGD Group 3

<400> SEQUENCE: 18

Arg Gly Asp Cys
 1

<210> SEQ ID NO 19
<211> LENGTH: 4
<212> TYPE: PRT
<213> ORGANISM: Artificial Sequence
<220> FEATURE:
<223> OTHER INFORMATION: RGD Group 4

<400> SEQUENCE: 19

Arg Gly Asp Val
 1

<210> SEQ ID NO 20
<211> LENGTH: 10
<212> TYPE: PRT
<213> ORGANISM: Artificial Sequence
<220> FEATURE:
<223> OTHER INFORMATION: RGD Group 5

<400> SEQUENCE: 20

Arg Gly Asp Ser Pro Ala Ser Ser Lys Pro
1               5                   10

<210> SEQ ID NO 21
<211> LENGTH: 5
<212> TYPE: PRT
<213> ORGANISM: Artificial Sequence
<220> FEATURE:
<223> OTHER INFORMATION: RGD Group 6

<400> SEQUENCE: 21

Gly Arg Gly Asp Ser
1               5

<210> SEQ ID NO 22
<211> LENGTH: 6
<212> TYPE: PRT
<213> ORGANISM: Artificial Sequence
<220> FEATURE:
<223> OTHER INFORMATION: RGD Group 7

<400> SEQUENCE: 22

Gly Arg Gly Asp Thr Pro
1               5

<210> SEQ ID NO 23
<211> LENGTH: 6
<212> TYPE: PRT
<213> ORGANISM: Artificial Sequence
<220> FEATURE:
<223> OTHER INFORMATION: RGD Group 8

<400> SEQUENCE: 23

Gly Arg Gly Asp Ser Pro
1               5

<210> SEQ ID NO 24
<211> LENGTH: 7
<212> TYPE: PRT
<213> ORGANISM: Artificial Sequence
<220> FEATURE:
<223> OTHER INFORMATION: RGD Group 9

<400> SEQUENCE: 24

Gly Arg Gly Asp Ser Pro Cys
1               5

<210> SEQ ID NO 25
<211> LENGTH: 5
<212> TYPE: PRT
<213> ORGANISM: Artificial Sequence
<220> FEATURE:
<223> OTHER INFORMATION: RGD Group 10

<400> SEQUENCE: 25

Tyr Arg Gly Asp Ser
1               5